US00PP10108P

United States Patent [19]

Trees

[11] Patent Number: Plant 10,108

[45] Date of Patent: Nov. 4, 1997

[54] GUINEA IMPATIENS NAMED 'BFP-650 PEACH'

[75] Inventor: Scott C. Trees, Arroyo Grande, Calif.

[73] Assignee: Ball Horticultural Company, West Chicago, Ill.

[21] Appl. No.: 685,536

[22] Filed: Jul. 24, 1996

[51] Int. Cl.[6] ..... A01H 5/00

[52] U.S. Cl. ..... Plt./87.6

[58] Field of Search ..... Plt./87.6

[56] References Cited

PUBLICATIONS

GTITM UPOVROM Listing for 'BFP–650 Peach' on application filed Jul. 5, 1996, Oct. 31, 1996.

*Primary Examiner*—James R. Feyrer

*Attorney, Agent, or Firm*—Burns, Doane, Swecker & Mathis, L.L.P.

[57] ABSTRACT

A new and distinct New Guinea Impatiens cultivar named 'BFP-650 Peach' is provided. This new cultivar was the result of a controlled breeding program wherein a plant designated '6468-2' (non-patented in the United States) was pollinated by a plant designated '380' (non-patented in the United States). The new cultivar forms large soft peach colored flowers having an eye of fuchsia and white that display an iridescent appearance. The foliage is dark bronze-green in coloration. An attractive compact upright mounded growth habit is exhibited. The new cultivar can be readily distinguished from the 'Bonfire Orange' cultivar (U.S. Plant Pat. No. 8,398).

1 Drawing Sheet

SUMMARY OF THE INVENTION

The present invention comprises a new and distinctive Impatiens plant, botanically known as New Guinea Impatiens, and hereinafter is referred to by the cultivar name 'BFP-650 Peach'.

The new cultivar is the product of a planned breeding program. More specifically, the breeding program which resulted in the production of the new cultivar was carried out in a controlled environment during 1993 at Arroyo Grande, Calif., U.S.A. The female parent (i.e., the seed parent) was a plant designated '6468-2' (non-patented in the United States) which exhibits red/white bicolored blossoms, and dark green foliage. The male parent (i.e., the pollen parent) was a plant designated '380' (non-patented in the United States) which exhibits orange blooms, dark green foliage, and a compact growth habit. The parentage of the new cultivar can be summarized as follows:

'6468-2'×'380'.

The seeds resulting from the above pollination were sown and plantlets were obtained which were physically and biologically different from each other. Selective study resulted in the identification of a single plant of the new cultivar. This plant initially was designated BFP-650.

It was found that the new cultivar of the present invention:

(a) exhibits attractive large soft peach flowers having an eye of white and fuchsia,
(b) forms dark bronze-green foliage,
(c) exhibits a good basal branching character, and
(d) exhibits a compact upright growth habit.

The plants of the new cultivar can be grown close together in the greenhouse.

Asexual reproduction of the new cultivar by terminal or stem cuttings taken during 1994, at Arroyo Grande, Calif., U.S.A. has demonstrated that the characteristics of the new cultivar as herein described are firmly fixed and are retained through successive generations of such asexual propagation.

The 'BFP-650 Peach' cultivar has not been observed under all possible environmental conditions to date. Accordingly, it is possible that the phenotype may vary somewhat with variations in the environment, such as temperature, light intensity, and day length.

When the new cultivar of the present invention is compared to the 'Bonfire Orange' cultivar U.S. Plant Pat. No. 8,398), it is found that the new variety exhibits larger flowers in greater numbers, and a more compact growth habit.

Plants of the new cultivar are marketed under the CELEBRETTE trademark by the Ball Horticultural Company.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at West Chicago, Ill., U.S.A.

DETAILED DESCRIPTION

The chart used in the identification of colors described herein is The R.H.S. Colour Chart of The Royal Horticultural Society, London, England. The plants were produced from cuttings taken from stock plants of the new cultivar and were transplanted during early November into 10 cm. (4 inch pots) and were grown in a soilless growth medium under standard greenhouse conditions at West Chicago, Ill., U.S.A. The greenhouse temperature was maintained at approximately 72° F. during the day and approximately 65° F. during the night. The plants were in flower eight to nine weeks later when the observations described hereafter were taken.

Botanical classification: *Impatiens hawkeri.*

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous, and branching.

Plant description:

*Form.*—Basal branching.

*Habit of growth.*—Compact upright mounded Internode lengths of approximately 2.5 to 2.8 cm. commonly are exhibited. A mature plant commonly measures approximately 8 to 8.6 cm. in height and approximately 21 to 22 cm. in width. This compares to a height of approximately 9 to 13 cm. and a width of approximately 25 to 30 cm. for the 'Bonfire Orange' cultivar.

*Foliage.*—The configuration is elliptic with an acuminate apex and an acuminate base. The mature leaves of the new cultivar measure approximately 7 to 11 cm. in length × approximately 2.8 to 4.0 cm. in maximal width compared to approximately 9.2 to 9.5 cm. in length × approximately 2.5 to 3.5 cm. in maximal width for the 'Bonfire Orange' cultivar. The leaf margins are serrate (as illustrated). The mature foliage of new cultivar is Green Group 136A with veins of Red-Purple Group 63A (adaxial), and Greyed-Purple Group 183C with a veins of Greyed-Purple Group 185B (abaxial). This can be compared to Yellow-Green Group 147A (adaxial) and Greyed-Purple Group 184A for the 'Bonfire Orange' cultivar. The stem coloration is Red Group 53B. This can be compared to Greyed-Purple Group 184A for the 'Bonfire Orange' cultivar.

Flower description:

*Flowering habit.*—Freely flowering.

*Natural flowering season.*—Throughout the year in a greenhouse environment.

*Flowers borne.*—Above foliage, arising from leaf axils.

*Flower color.*—The superior petal is Red Group 41A at the outer edge and Red-Purple Group 63D at the base. The other four petals have edges of Red Group 41A which fades to Red-Purple Group 63D and becomes Red-Purple Group 63A at the base (adaxial) and Red Group 40C with a midvein of Red-Purple Group 63A (abaxial). This can be compared to Orange-Red Group 33A (adaxial) and Orange-Red Group 32B (abaxial) for the 'Bonfire Orange' cultivar.

*Quantity of flowers.*—Approximately 7 to 9 per axil for the new cultivar. This can be compared to approximately 4 to 6 per axil for the 'Bonfire Orange' cultivar.

*Number of petals.*—Five, and overlapping.

*Petal shape.*—Heart-shaped, with the upper three petals commonly having broader bases than the lower two petals.

*Flower size.*—Approximately 5.3 to 6 cm. in length and approximately 5.3 to 6 cm. in width. This can be compared to approximately 4.7 to 5 cm. in length and approximately 4.7 to 5 cm. in width for the 'Bonfire Orange' cultivar.

*Flower buds.*—Ellipsoidal in configuration, and generally covered with three sepals plus two rudimentary sepals fused into the under surface of the superior petal. A spur originating from the base of the inferior sepal is approximately 4 to 4.5 cm. in length on fully opened flowers which can be compared to approximately 4.5 to 4.7 cm. for the spur length of the 'Bonfire Orange' cultivar. The spur coloration is Red Group 63A for the new cultivar. This can be compared to a spur coloration of Red Group 47B for the 'Bonfire Orange' cultivar.

*Reproductive organs.*—The three inferior stamens are Red Group 46B. The anthers tend to be fused together forming one organ that surrounds the pistil. Commonly the anthers shed pollen prior to the stigma becoming receptive. The pollen coloration is Yellow Group 11C and the ovary coloration is Yellow-Green Group 144A for the new cultivar. This can be compared to a stamen coloration of Red-Purple Group 63B, a pollen coloration of White Group 155D, and an ovary coloration of Yellow-Green Group 144B for the 'Bonfire Orange' cultivar.

I claim:

1. A new and distinct cultivar of New Guinea Impatiens plant named 'BFP-650 Peach', substantially as herein shown and described, which:

(a) exhibits attractive large soft peach flowers having an eye of white and fuchsia,
(b) forms dark bronze-green foliage,
(c) exhibits a good basal branching character, and
(d) exhibits a compact upright growth habit.

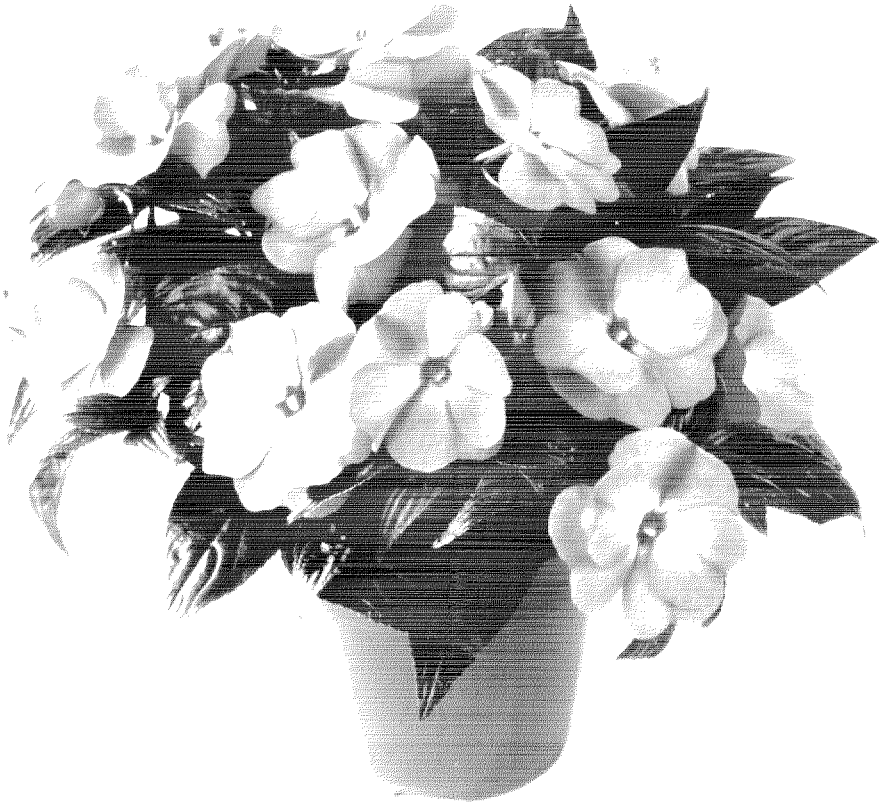

* * * * *